US011766524B2

(12) United States Patent
Brunner

(10) Patent No.: US 11,766,524 B2
(45) Date of Patent: Sep. 26, 2023

(54) DEVICE AND METHOD FOR HIGH-CONTROL-STEERABLE TIP NEEDLES HAVING RUDDER/KEEL AND TIP STEERING/ANGLE CHANGING MEANS

(71) Applicant: Jasperate, Inc., Lisle, IL (US)

(72) Inventor: Charles S. Brunner, Stockton, NJ (US)

(73) Assignee: Jasperate, Inc., Lisle, IL (US)

( * ) Notice: Subject to any disclaimer, the term of this patent is extended or adjusted under 35 U.S.C. 154(b) by 626 days.

(21) Appl. No.: 16/840,569

(22) Filed: Apr. 6, 2020

(65) Prior Publication Data
US 2020/0316310 A1 Oct. 8, 2020

Related U.S. Application Data

(60) Provisional application No. 62/830,986, filed on Apr. 8, 2019.

(51) Int. Cl.
*A61M 5/32* (2006.01)
*A61M 5/158* (2006.01)
*A61M 25/01* (2006.01)

(52) U.S. Cl.
CPC ............ *A61M 5/329* (2013.01); *A61M 5/158* (2013.01); *A61M 5/32* (2013.01); *A61M 5/3287* (2013.01); *A61M 25/0105* (2013.01); *A61M 25/0133* (2013.01); *A61M 2005/3289* (2013.01)

(58) Field of Classification Search
CPC ........ A61M 5/329; A61M 5/158; A61M 5/32; A61M 5/3287; A61M 25/0105; A61M 25/0133; A61M 2005/3289
See application file for complete search history.

(56) References Cited

U.S. PATENT DOCUMENTS

| | | | |
|---|---|---|---|
| 2012/0197190 A1* | 8/2012 | Suon | A61M 25/0113 604/95.04 |
| 2012/0265132 A1* | 10/2012 | Nomura | A61B 1/00098 604/95.04 |
| 2016/0317760 A1* | 11/2016 | Centeno | A61B 17/3421 |
| 2017/0354416 A1* | 12/2017 | Dickinson | A61B 34/20 |
| 2019/0091438 A1* | 3/2019 | Higgins | A61M 25/10 |
| 2019/0351180 A1* | 11/2019 | Ryu | G01L 1/246 |

* cited by examiner

*Primary Examiner* — Dung T Ulsh
(74) *Attorney, Agent, or Firm* — Latimer LeVay Fyock LLC

(57) ABSTRACT

A system of needles having rudders or keels is provided having perforations, such as kerfs, to allow the needles to be bent by the manipulations of wires imbedded within the needle body. The pulling or pushing of the embedded wires, or stylets, causes the needle tip to be bent, while within the body, to allow the needle to be steered past impediments towards the target necessitating treatment. Wires can be pulled or pushed and in some instances both a push and pull wire are provided to give the needle precision steerability. The needles are provided with a keel or rudder, or can be shaped such as with a teardrop cross-section, to give a degree of stabilization to the course the needle, and attendant tubing, takes within the patient. The kerf cut section of the needle, which can be on one side, two sides or all about the circumference of the needle, allows the needle to be bent one way and then, as needed, another way to allow the needle to be steered within the body.

1 Claim, 16 Drawing Sheets

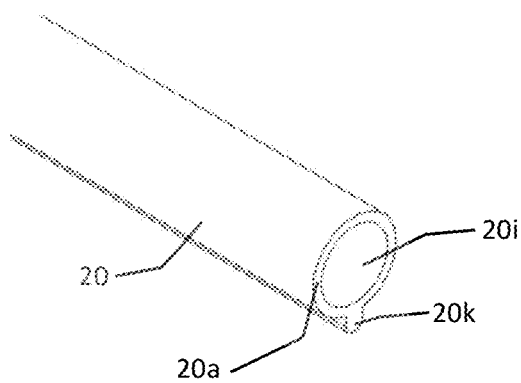
FIG. 3A
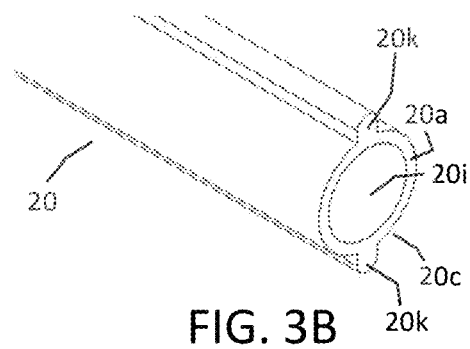
FIG. 3B
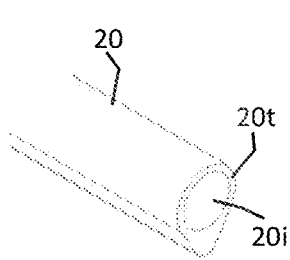
FIG. 3C
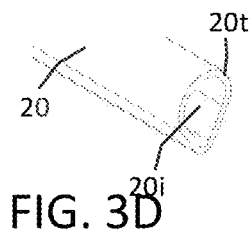
FIG. 3D
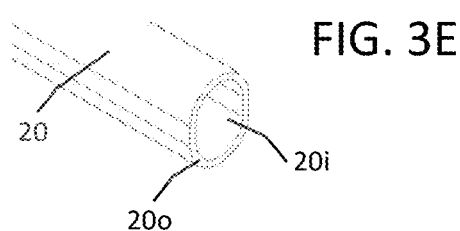
FIG. 3E
FIG. 3

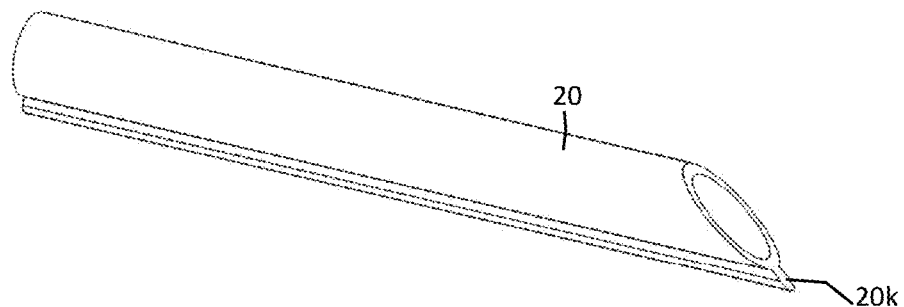
FIG. 4A
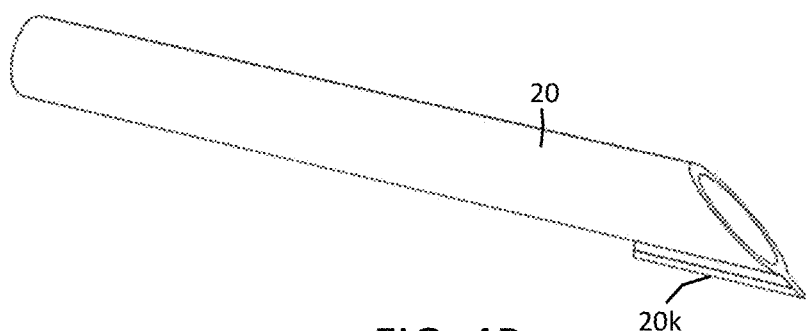
FIG. 4B
FIG. 4

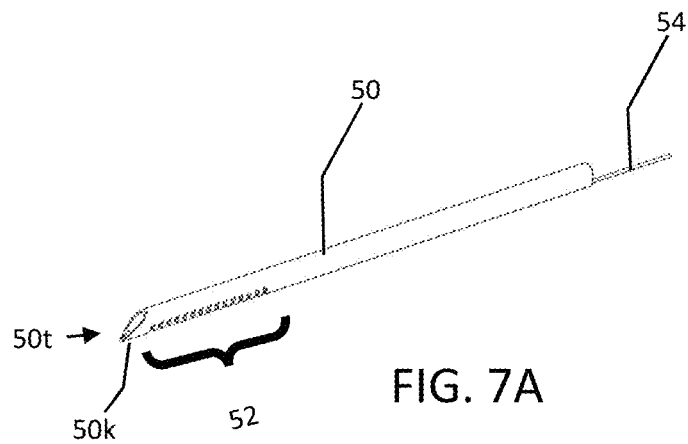
FIG. 7A
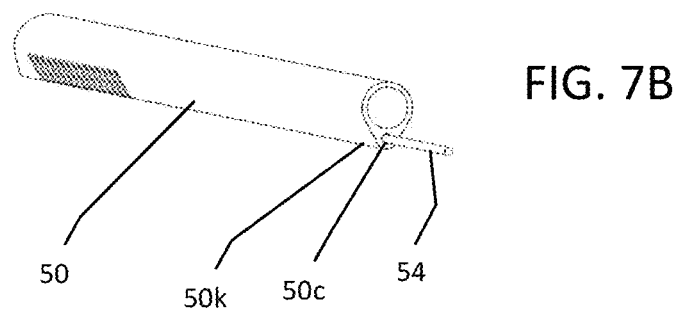
FIG. 7B
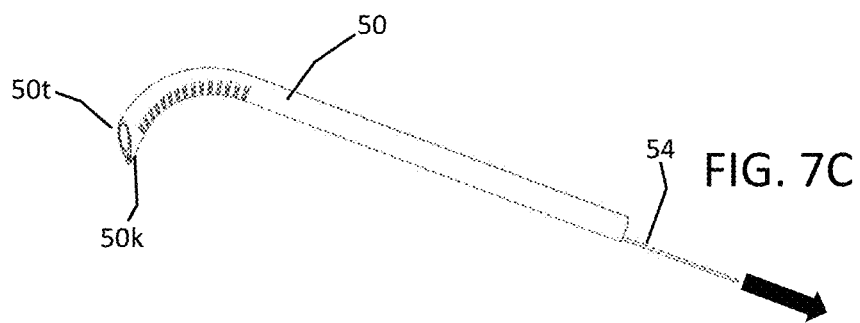
FIG. 7C
FIG. 7

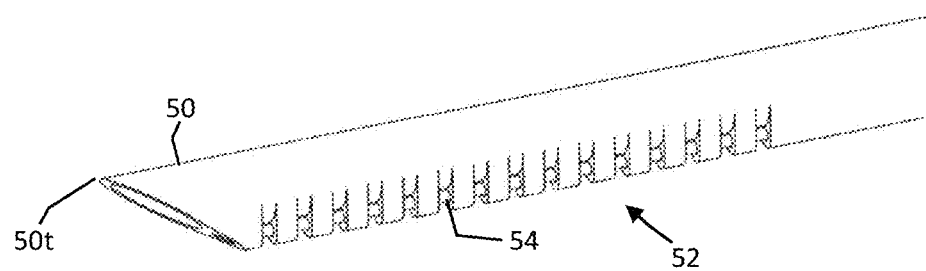
FIG. 8A
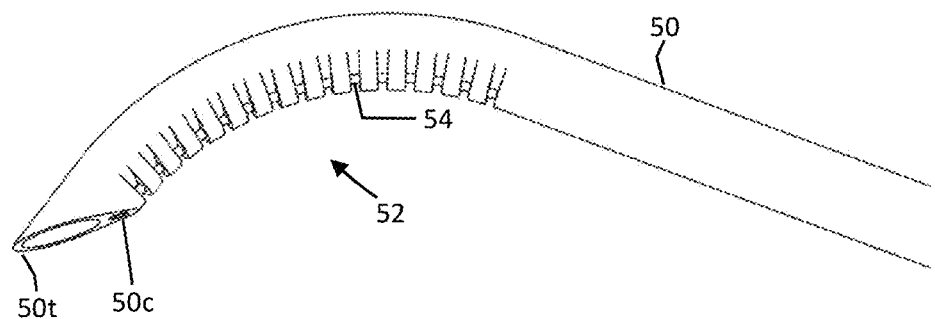
FIG. 8B
FIG. 8

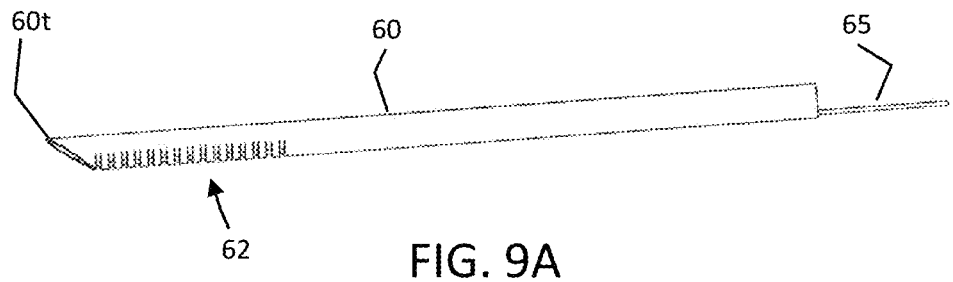
FIG. 9A
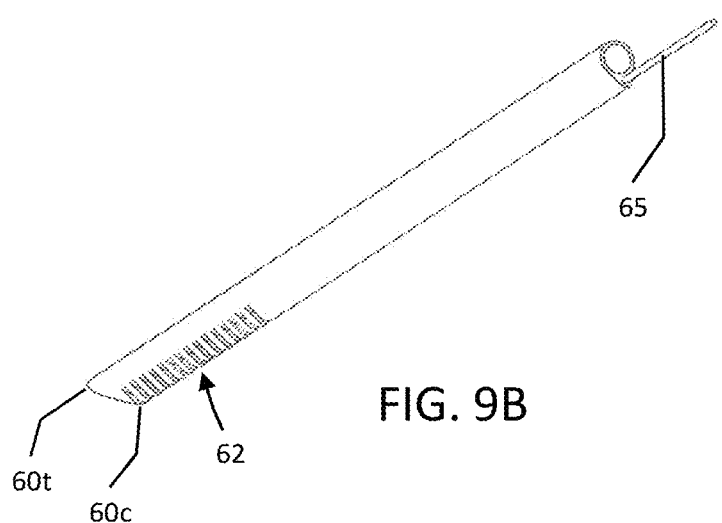
FIG. 9B
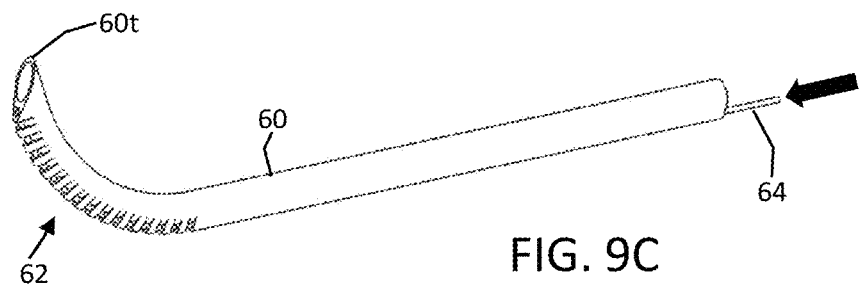
FIG. 9C
FIG. 9

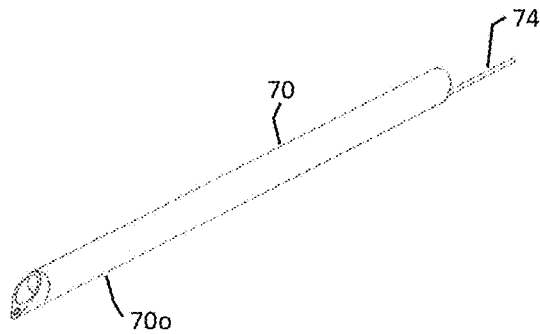
FIG. 10A
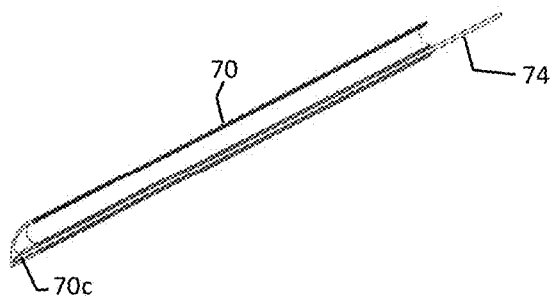
FIG. 10B
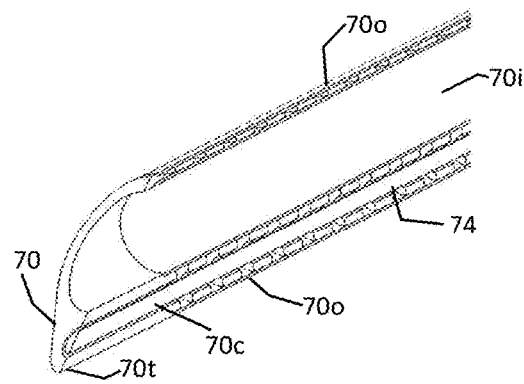
FIG. 10C
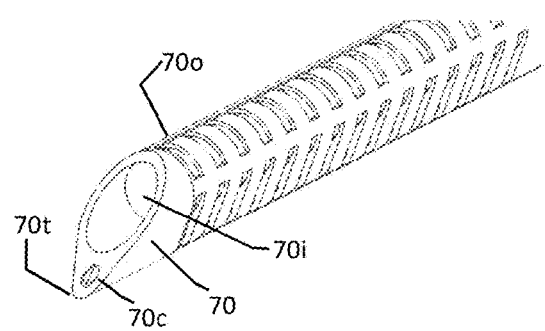
FIG. 10D
FIG. 10

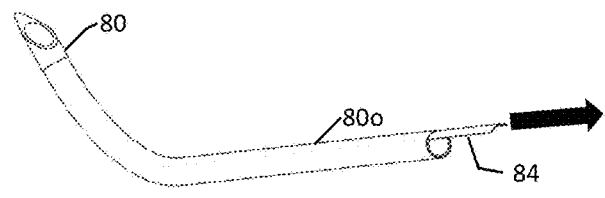
FIG. 11A
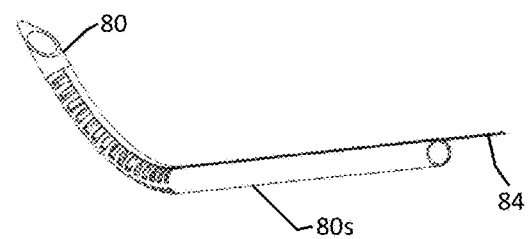
FIG. 11B
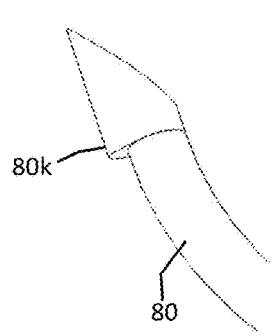
FIG. 11C
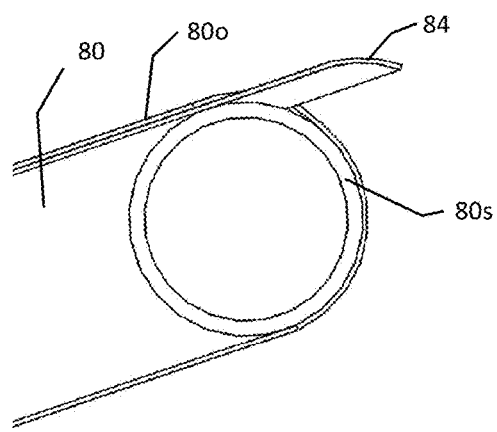
FIG. 11D
FIG. 11

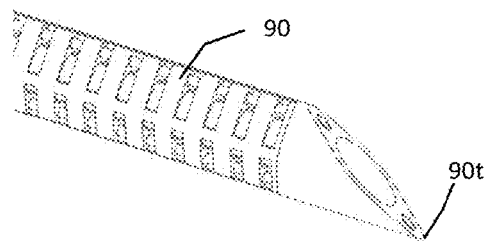
FIG. 12A
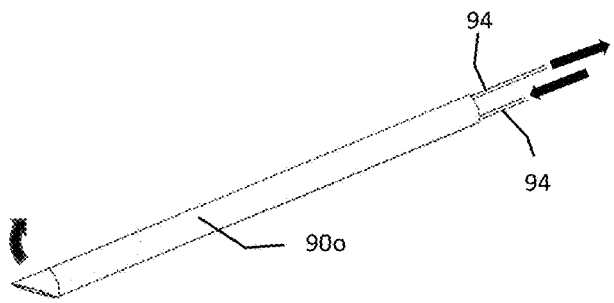
FIG. 12B
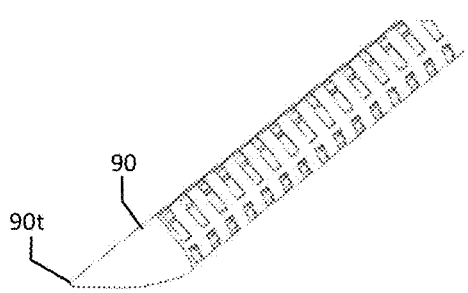
FIG. 12C
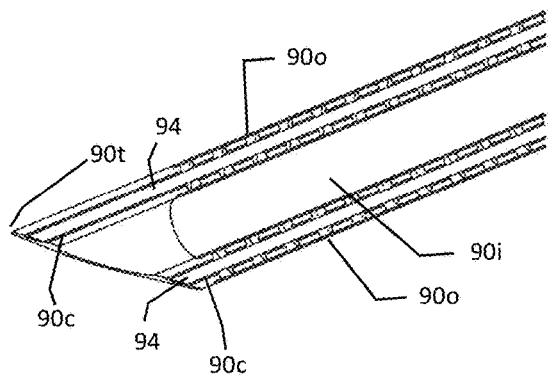
FIG. 12D
FIG. 12

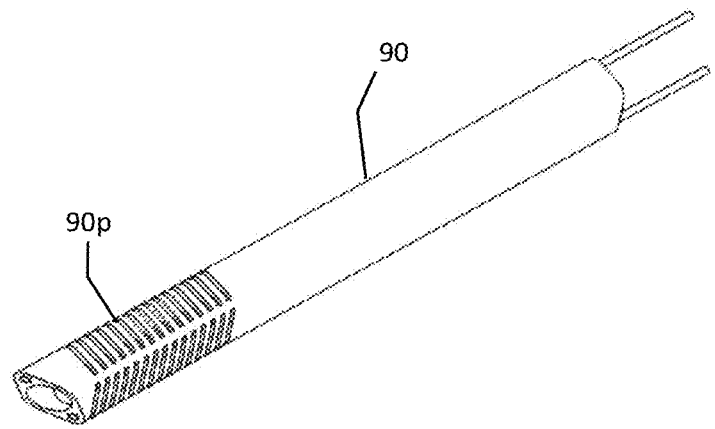
FIG. 13A
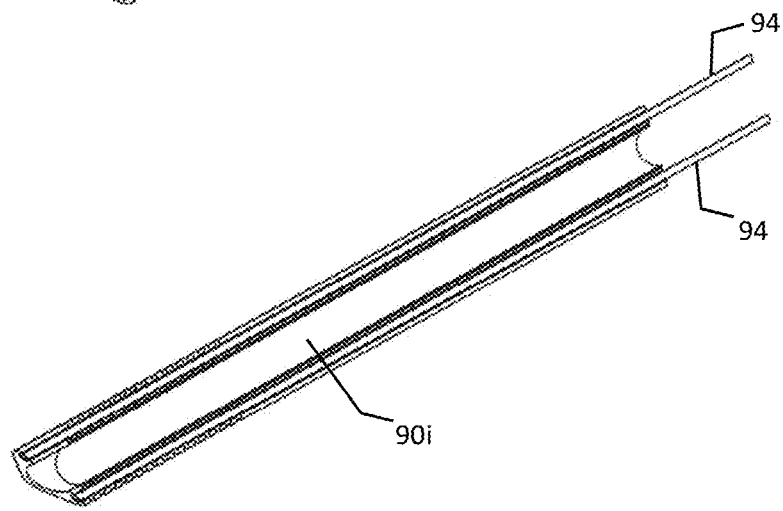
FIG. 13B
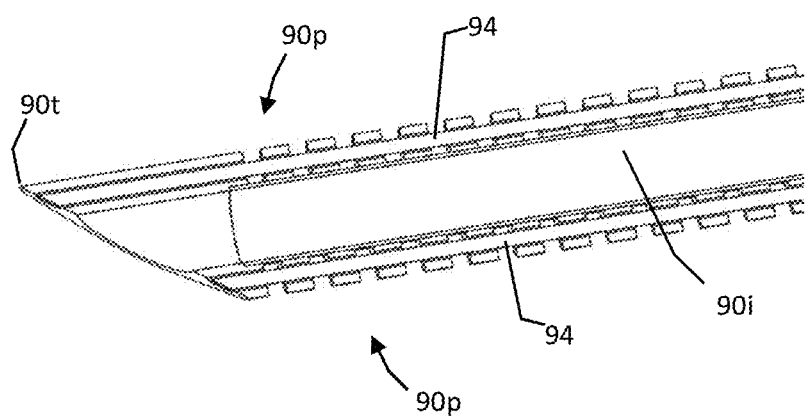
FIG. 13C
FIG. 13

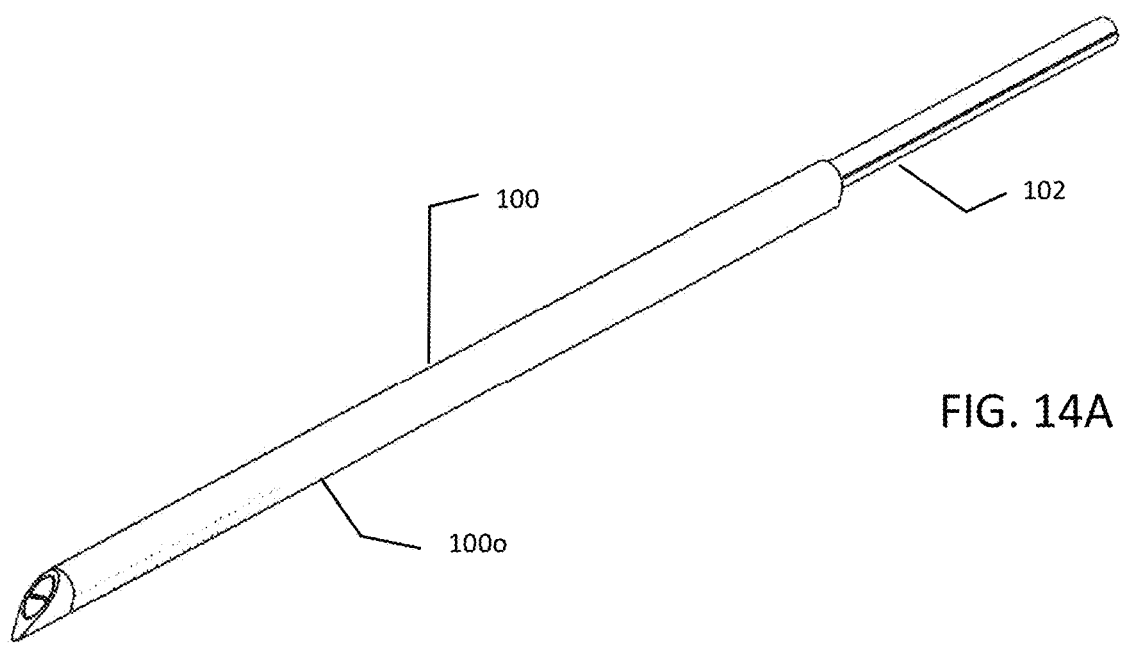
FIG. 14A
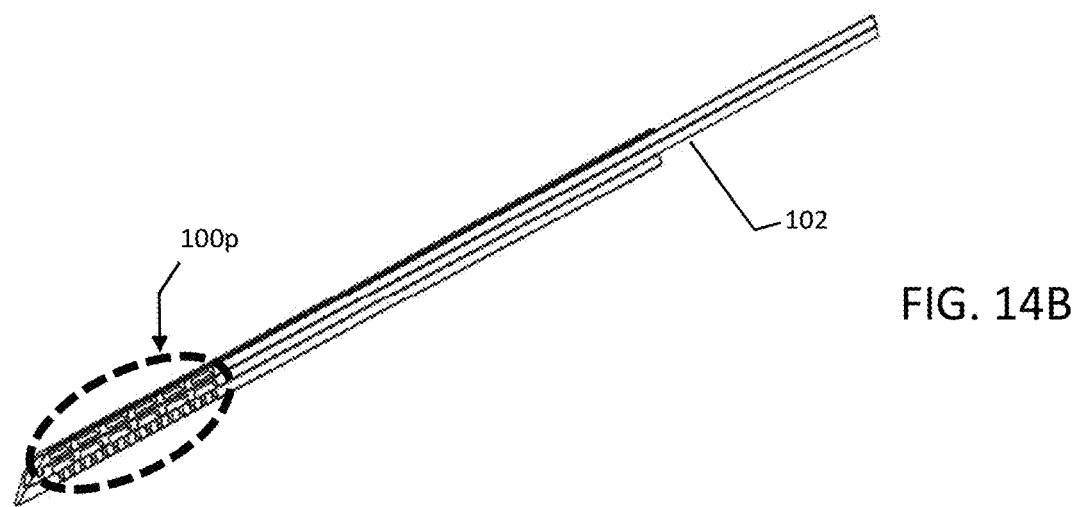
FIG. 14B
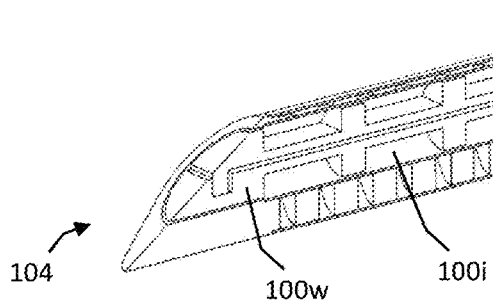
FIG. 14C
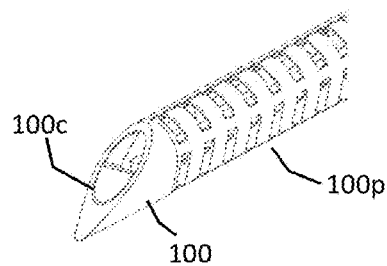
FIG. 14D
FIG. 14

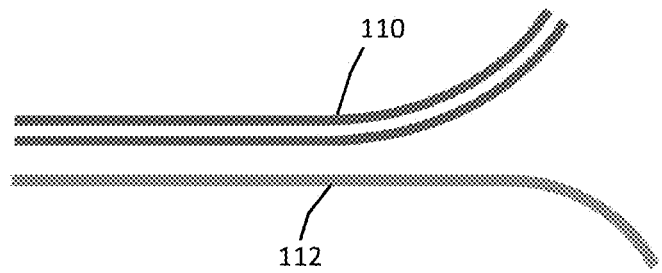
FIG. 15A
FIG. 15B
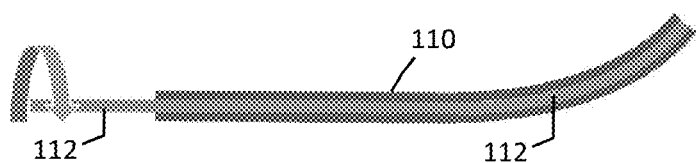
FIG. 15C
FIG. 15

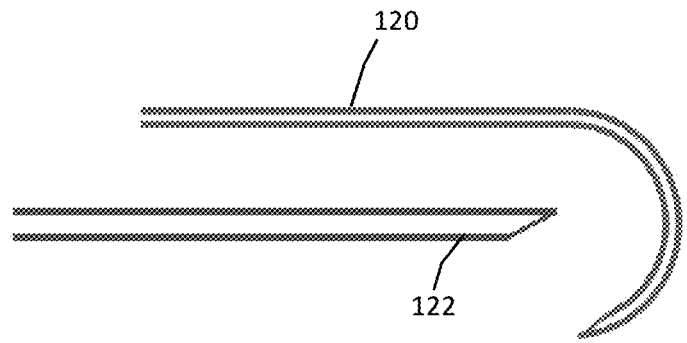
FIG. 16A
FIG. 16B
FIG. 16C
FIG. 16

DEVICE AND METHOD FOR HIGH-CONTROL-STEERABLE TIP NEEDLES HAVING RUDDER/KEEL AND TIP STEERING/ANGLE CHANGING MEANS

FIELD OF THE INVENTION

The present invention concerns needles and attendant equipment to both insert and remove fluids (liquids and/or gasses) and suspended solids from a body and the method of using such equipment. More particularly the present invention concerns a new and novel device that both provides improved control, steer-ability and interchangeability of the tip angle of such devices.

BACKGROUND OF THE INVENTION

Health care workers, and most particularly those that are Rheumatologist and Interventionists, do a significant number of treatments, pain management exercises and the like using syringes and hypodermic needles to inject medicaments into the body. For example, trigger finger can be treated by injecting medication between the A1 pulley and its associated tendon. For back pain, medication is injected at various locations along and around the spine. In both, and in other instances, accessing the target for injection of the medicine may be difficult due to impediments located between the point of entry into the body and the target of the treatment; any obstructions that may internally, lie along the straight line access, or externally prevent direct access to the point of entry will be problematic. Obstructions can, among other things, be objects that are impenetrable by the needle or can be such things as sensitive body elements, when the body is a human or animal body for example, such as nerve bundles, veins and arteries or the like, that if punctured or severed could lead to complications in the treatment or effect the wellbeing of the patient.

Jasperate, Inc. of Illinois, the assignee of the present invention, has developed such devices as pre-bent needles and needles that can have their directional angle changed relative to the axis of the needle hub and syringe. The present invention addresses many situations that are encountered with external obstructions to the entry point that will limit the ability to properly reach the target point.

One problem encountered during the procedures described above, particularly when having to navigate through thicker layers of fat and muscle, again in the example case where the body is animal in nature, is to guide/steer the needle tip to the proper location. Current methods of steering a needle past an impediment involve the operator creating a slight bend of the needle to help stabilize the needle as it is inserted; such a bend also allows the operator to subsequently spiral the needle through the tissue to the desired target point. While this is the current state of the art, there is a desire to have improved control and stability while inserting the needle than that offered by typical generally cylindrical hypodermic needles.

SUMMARY OF THE INVENTION

The present invention provides a needle system having a steerable tip to allow the needle to be guided around impediments and steered to the location, within a body, for treatment. The term "body" here is meant to include anything that the system is used on, including human bodies, animal bodies and any mass in which the system might be used. To create the system, a needle having a hollow shaft, forming the longitudinal axis of the needle is provided having a tip at the distal end of the hollow shaft and a bendable segment of the shaft, the bendable segment being adjacent the tip. In some embodiments, in order to assist in steering the needle within the body, the needle has a keel, or rudder, segment depending from the hollow shaft, along at least a segment of the shaft. The keel or rudder has a channel therethrough and an actuation element is attached to the tip of the needle and is then housed within the channel in the keel or rudder segment; the wire then extends out from the proximal end of the needle, such that when the portion of the wire extending out of the distal end of the needle is either pulled or pushed, in a direction generally parallel to the axis of the needle, the bendable segment of the needle is caused to bend, thereby changing the directional angle of the needle tip relative to the longitudinal axis of the needle. It will be understood that while a keel/rudder is desired, needles made in accordance with the present invention can be created and the method practiced without a keel/rudder, without departing from the novel scope of the present invention.

In one embodiment, the wire can be replaced with a resilient ribbon, a flat wire or a split stylet, which has similar to identical characteristics to the wire, Persons having ordinary skill in the art will understand that any means to aid in the steering of the needle by a member that extends from the needle to the exterior can be substituted without departing from the novel scope of the present invention.

In a preferred embodiment of the needle system the needle includes an inner surface and an outer surface and the bendable segment of the shaft is created by cutting material from the outer surface of the needle. This cutting of material is done in the manner of a kerf to create the bendable segment. In one embodiment the wire is pretensioned such that releasing the wire causes the needle to bend at the bendable segment; in another embodiment the wire is attached in the needle such that pulling the wire causes the needle to bend.

In some embodiments, the needle system can included a second keel or rudder having a second channel therein with a second wire attached to the tip and placed within the second channel, such that the bending of the tip relative to the shaft can be more precisely controlled by pulling or pushing on one or both wires. In some such systems, the first wire can be pulled and the second wire pushed to control the direction of the needle, or vice versa. Further, such systems can include a stylet, at the proximal end of the shaft, for anchoring the proximal ends of the first and second wire, such that twisting the stylet clockwise causes the tip to bend in one direction and twisting the stylet counterclockwise causes the needle to bend in another direction.

The present invention further includes a method of steering a needle past an impediment within a body, and includes the steps of providing a needle system as described above wherein, when the needle is pushed into a body, it can be steered by pulling or pushing the wire, to effect a bend of the tip, and then driving the needle in the direction of the bend. In one embodiment, the method of steering a needle past an impediment within a body includes the step of providing a needle system with a first and second wire, and attendant elements as described above and wherein when the needle is pushed into a body, it can be steered by pulling or pushing one or both of the first wire or second wire and then driving the needle in the direction of the bend. In any such embodiment, the method can include having a needle with a stylet at the proximal end of the shaft, for anchoring the ends of the first and second wire therein. The method is improved as steering is effected by twisting the stylet; for example a clockwise twist of the stylet would cause the tip to bend in one direction then twisting the stylet counterclockwise would cause the needle to bend in another direction. Effectively, the operator drives the tip of the needle as one would steer a vehicle.

It will be understood, by persons having ordinary skill in the art, that one aspect of the present invention is to provide a rudder or keel that protrudes from the OD of the needle and enhances the control of the needle tip as the needle is inserted. Further, the rudder or keel of the needle can be the full length of the needle or just near the tip of the needle. Further, there may be one or more than one protrusions around the circumference of the needle outer diameter. While instantiations of the rudder or keel can be protrusions around the circumference of the needle, control, as desired, can also be achieved by creation of a non-circular needle, for example a needle with an oval or teardrop shaped cross section. The rudder or keel element can be integrated into a straight needle that is subsequently bent by the doctor, practitioner, nurse, medic or other person operating the device and method of the present invention and hereinafter referred to as the operator, at the time of use, or it can be on a pre-bent needle that is supplied by the manufacturer. This variety of configurations provides the operator with a choice of solutions and allows for the selection of the most appropriate needle for the requirements of any given procedure.

In summary, then, even with enhanced position control provided by the addition of the rudder/keel, there are still situations where the target is still obstructed either by vasculature, bone, nerves or just difficult tissue. For example, which example is not meant to be limiting, if the target of interest is on the side or front of the spine, or to the front side of a bony protrusion of the vertebrae, or a target that is within a tunnel like structure in the spine where the tunnel is open on the side (where straight line access would be through the front of the body and would involve going through the belly for example), it will be virtually unreachable or require inordinate skill to reach. In such cases(s), it would be desirable to have a straight or slightly bent needle that can be inserted at a position close to the target, in this case making use of the enhanced control provided by a rudder. With the target area close at hand, the operator can actuate the bending of the needle tip to access the difficult to reach target point. It will be understood that continued needle insertion may occur at the same time that the bending is occurring or the insertion depth may stay constant such that the bending creates a path through the tissue.

Actuation of the bend in the hypodermic needles, as taught herein, can be achieve through a number of different innovative and novel means. In some instances, the rudder/keel feature(s) of the present invention can be used to provide a channel(s) and supporting structure(s) for the actuation element. In other cases, the multi-layer construction of the needle of the present invention can provide a path for the actuation element. In yet other cases the Stylet can be used to actuate and/or activate the bend of the needle.

It should be noted, however, that in some cases the steerable/changeable tip angle needle can be incorporated without a rudder or keel; that is, the rudder/keel does not need to be integral to this aspect of the invention. It should also be noted that the present invention allows for a needle to be shipped in a straight configuration, the operator can then put a desirable tip angle/bend in place to help guide/spiral the needle to the target and subsequently provide for actuation/activation of a greater tip angle/bend to finalize tip placement at the target.

It is therefore an object of the present invention to provide a means for better control of the process of injection and suction with a rudder and or keel and changes to the steer-ability and change of tip angle as will be disclosed herein. Other objects and advantages of the present invention will become apparent as the description proceeds. A more detailed explanation of the invention is provided in the following description and claims and is illustrated in the accompanying drawings.

The present invention will be summarized and explained in this application in coordination with images and discussion of the images on the drawing sheets. Persons having ordinary skill in the art will understand that this is the most expedient manner of disclosure in this type of application.

BRIEF DESCRIPTION OF THE DRAWINGS

FIGS. 3A-3E show a number of examples of a needle having a rudder as disclosed in the present invention and a needle without a rudder.

FIGS. 4A-4B show at least two different lengths of rudder useable in the needle of the present invention, with any length between the shown images possible

FIGS. 7A-7C show images of a needle have a rudder and channel and having means to bend a portion of the needle to facilitate steering the needle as desired.

FIGS. 8A-8B illustrate the manner in which the needles of FIGS. 7A-7C can be bent to facilitate steering the needle.

FIGS. 9A-9C illustrate a method of remotely bending a needle, of the type shown in FIGS. 7A-7C, during use.

FIGS. 10A-10D are illustrative of the needles of FIGS. 9A-9C along with other means to effect the bend and steer the device of the present invention.

FIGS. 11A-11D are illustrative of the needles of FIGS. 9A-9C along with other means to effect the bend and steer the device of the present invention.

FIGS. 12A-12D are illustrative of the needles of FIGS. 9A-9C along with other means to effect the bend and steer the device of the present invention.

FIGS. 13A-13C are illustrative of the needles of FIGS. 9A-9C along with other means to effect the bend and steer the device of the present invention.

FIGS. 14A-14D are illustrative of the needles of FIGS. 9A-9C along with other means to effect the bend and steer the device of the present invention.

FIGS. 15A-15C are illustrative of the needles of FIGS. 9A-9C along with other means to effect the bend and steer the device of the present invention.

FIGS. 16A-6C are illustrative of the needles of FIGS. 9A-9C along with other means to effect the bend and steer the device of the present invention.

DETAILED DESCRIPTION OF THE ILLUSTRATIVE EMBODIMENT

Figure 1:
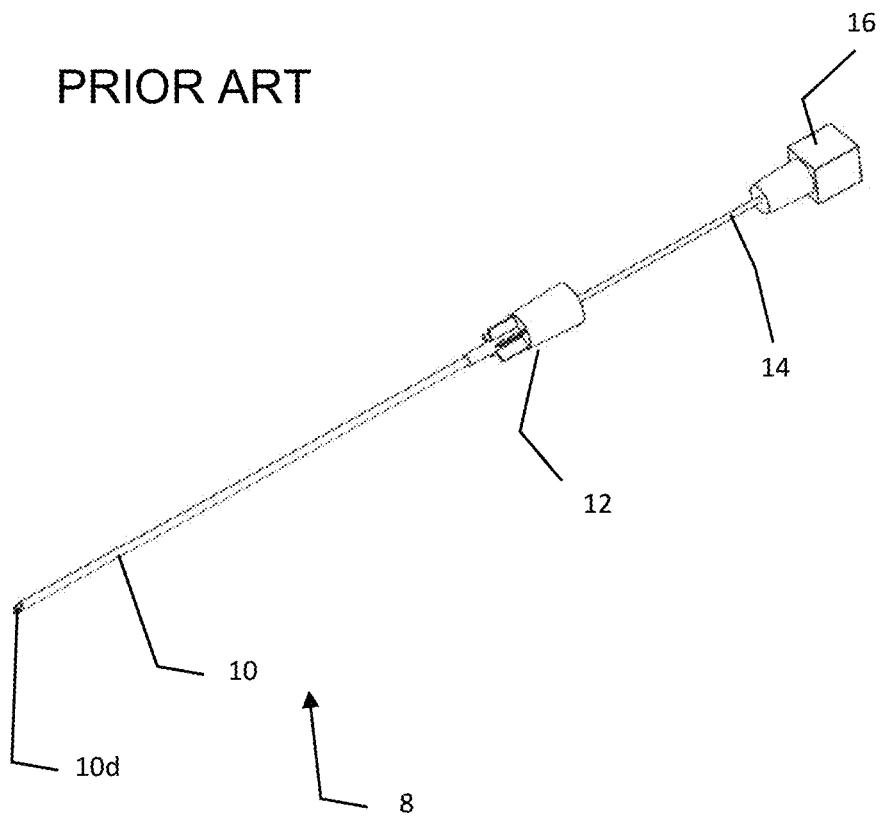
FIG. 1 is a perspective view of a needle and stylet of the prior art.

While the present invention is susceptible of embodiment in various forms, there is shown in the drawings a number of presently preferred embodiments that are discussed in greater detail hereafter. It should be understood that the present disclosure is to be considered as an exemplification of the present invention, and is not intended to limit the invention to the specific embodiments illustrated. It should be further understood that the title of this section of this application ("Detailed Description of the Illustrative Embodiment") relates to a requirement of the United States Patent Office, and should not be found to limit the subject matter disclosed herein.

Figure 2:
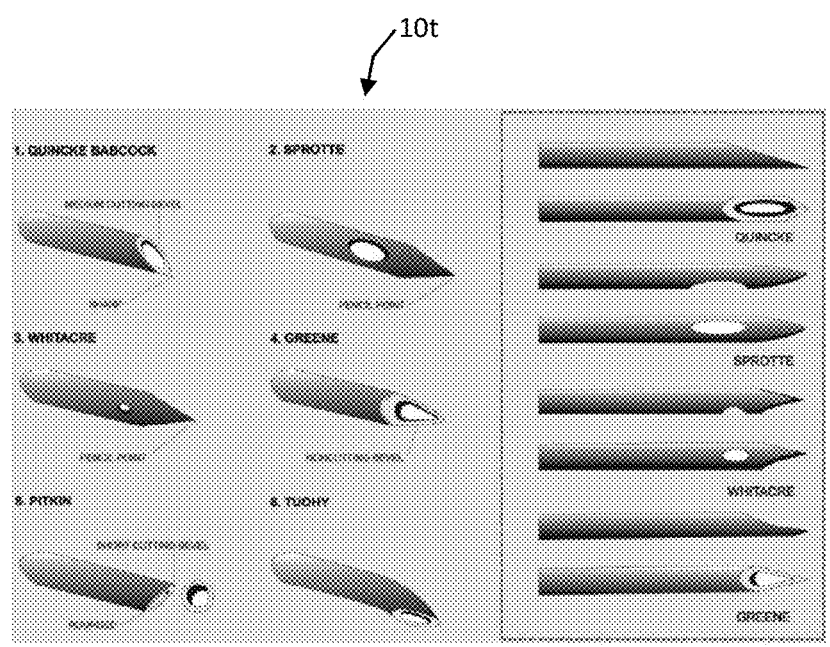
FIG. 2 is a table of the numerous needle tip types that can be used with the present invention.

Referring to the drawing figures, FIG. 1 shows a standard needle system 8 of the prior art, including a hollow needle 10, a hub 12, a solid wire 14, held within the hollow needle 10 by hub 12 and a stylet hub 16, which completes the needle system 8 and helps hold all the parts thereof together (for attachment to a syringe or other medical device, not shown). In some needle systems 8 the stylet can be used to rotate the wire within needle 10 and move wire 14 in and out of the distal end 10d of needle 10. It will be seen in FIG. 2, that there are many types of needle tips 10t possible at the distal end 10d of needle 10; such tips are used for various types of treatments and procedures and are well known to persons having ordinary skill in the art. These needle ends are displayed here so as to introduce the ends of standard needles so as to contrast them with the needle(s) of the present invention, as disclosed below.

Referring now to FIG. 3, the shafts 20 of variously shaped needles are shown. As shown in FIG. 1, the typical prior art shaft of a needle generally has a circular cross section 20a. FIG. 3A shows a typical circular cross section needle shaft 20, with a single keel 20k created thereon; FIG. 3B shows a typical circular cross section needle shaft 20, with a keel 20k located at two points along the circumference 20c of the needle. While FIG. 3B shows two keels 20k located 180 degrees apart, it will be understood that such keels 20k can be placed at any points on the circumference as needed and that while two keels 20k are show, any number of keels 20k can be included as needed or desired to better complete a medical task. Referring now to FIG. 3C, a generally circular cross section needle shaft 20 is shown with a keel 20k that has been created into a generally tear drop shape; it will be seen that the cross sectional area 20a of the needle of FIG. 3C remains the same as the generally circular cross sectional area 20a needle 20 shown in the prior two images. The needle 20 of FIG. 3D, in contrast to that of FIG. 3C, shows a tear dropped shaped cross sectional needle having a cross sectional area 20t increased in size by having the keel area included as part of the open interior 20i of the needle. Such a needle provides a greater flow of fluids or solids, in or out of the needle, while having a cross sectional shape identical to that of the needle 20 of FIG. 3C. FIG. 3E shows another embodiment of the needle, where the shape is oval and the cross-sectional area is shown as 20o; such a needle would have a similar, but not exact, cross section to that of the needle of FIG. 3B, with more flow volume.

Referring now to FIG. 4, a perspective view of two needle segments FIGS. 4A and 4B, each showing that the keel 20k can be made to varying lengths, depending on the need and use for which the needle 20 is made. FIG. 4A shows a keel 20k along the full length of the needle and FIG. 4B shows a keel 20k at just the very tip of the needle 20. It will be understood by persons having ordinary skill in the art that the length of the keel 20k can be of any length therebetween as desired and needed.

Figure 5:
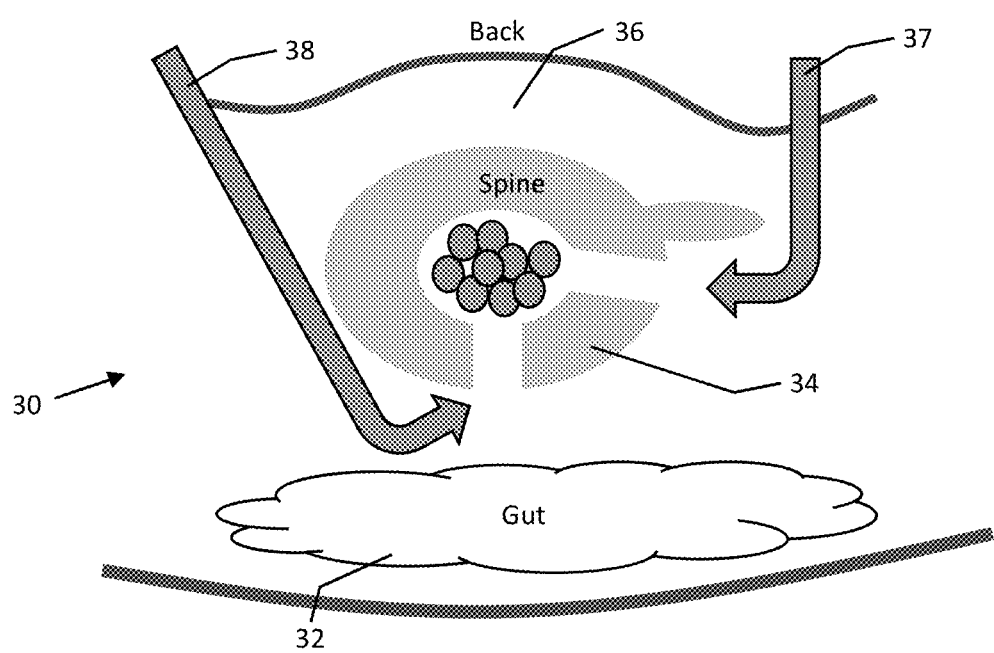
FIG. 5 is an illustration of a potential difficult to reach situation in a body, for which the present invention is designed to overcome.

As shown in FIG. 5, the use of a steerable needle can be useful to reach a part of the body, which in the case of the cross-section view of the torso 30, shown therein may be made difficult by the natural placement of the elements of the body. In the example shown, it is desired to have some procedure directed to the nerves within the spine. The anatomy of the patient provides natural barriers to injection, including the gut or belly 32 section of the body, the spinal column and its bony segments 34 and the musculature 36 of the back of the body. A needle that can be steered can be introduced at a convenient and less damaging part of the body 30, as shown by arrows 37 and 38 and then steered, using visual techniques, including x-rays and other, to place the needle in the appropriate location to effect the procedure prescribed.

Figure 6:
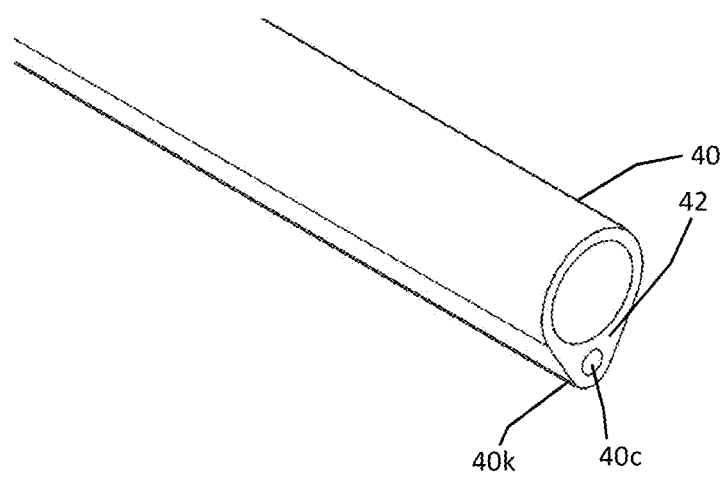
FIG. 6 is a perspective view of a needle having a rudder and an actuation channel of the present invention.

In an embodiment of the present invention, as shown in FIG. 6, a needle 40 having a circular cross-section through area 42 and an overall tear drop shaped cross-section formed keel 40k. It will be seen that the keel 40k further comprises an actuation channel 40c and it will be understood that the channel can be used to provide a path and structural support for an actuation cable, wire or filament 40w. FIG. 7 is a perspective view of a needle 50 made in accordance with the needle 40 shown in FIG. 6. FIG. 7A shows the needle 50 in its initial straight condition; it will be seen that there is included on the needle a bending section 52 that is created by the removal of material from the keel 50k, such as by kerfing. Those having skill in the art will note that the bending section 52 of the needle, that will have the most flexibility in steering, is made such that the bend can achieve a generally 90 degree curvature. Those having ordinary skill in the art will also understand that while cutting or kerfing is described as a method of creating the weakened section of the needle, to permit the bending described herein, any method of creating such a weakened section, including cutting or creating such section with molds or matrices or, or by material selection, or other manners as known by persons having ordinary skill in the art, can be used herein without departing from the novel scope of the present invention.

It will be seen that needle 50 further comprises a wire 54, which as shown in FIG. 7B, is carried within an actuation channel 50c, and is anchored generally near the tip 50t of needle 50. With such anchorage, wire 54, extending from the tip 50t of needle 50 and out of the needle, can be made to such length as to allow the operator to pull the wire causing tip 50t of needle 50 to bend as shown in FIG. 7C. FIGS. 8A and 8B more closely show the bending section 52 of needle 50, for closer examination. Most importantly, wire 54 can be seen within needle 50 at the kerfed portions of the needle body. Importantly, it will be understood by persons having ordinary skill in the art that the needle tip 50t can be made in any manner currently known and that the needle bevel can be either facing the point where the wire is attached or can be opposite from the point of pull/press of the wire as desired by the operator. Such manufacture will be true for any configuration of the present invention.

In addition to a needle 50 that can be pulled to effect a bend to provide steerability, it will be understood, in viewing FIG. 9, that a more rigid wire (as compared to the wire used in the prior example) 65 can be used in a needle 60, having characteristics similar to those described above for needle 50, with the wire being pushed to cause the bend. This can be seen as a pre-tensioned needle that is then released from tension to affect the desired bend. In such configuration, it will be understood that the elasticity of the system can be employed to do the bulk of the work in bending the needle. In the case of a pre-bent needle, the needle can be held straight by pulling on the wire, bending then occurs when the wire is released (or the tension thereon is lessened).

Referring now to FIG. 10, there is shown another embodiment of the needle 70 of the present invention. In this embodiment the needle is a needle having a flexible inner sleeve 70*i* and a flexible outer sleeve 70*o*. The needle 70 in this embodiment is a composite of a rigid or semi-rigid material, such as steel, plastic, carbon fiber or metallic alloys as non-limiting examples, with flexible inner and outer sleeves. In this embodiment, the needle is perforated, as for example by kerfing, on two opposed sections of the circumference at the desired bending points; thereby allowing for the bending of the needle 70 with less force. Similar to the prior embodiments, a wire 74 is fixed with in actuation channel 70*c*, best shown in the cross-sectional image FIG. 10C. It will be understood by persons having ordinary skill in the art, that the needle here can be pulled or pushed to create the desired bend and steerability. In other embodiments of the present needle 70, the needle can be created alternately with an inner sleeve alone or with an outer sleeve alone or both, as shown.

Referring now to FIG. 11, another embodiment of the needle 80 of the present invention is shown. In this embodiment, a flat actuator 84 has been substituted for a wire, as in the prior embodiments. In the present embodiment, the actuator 84 is shown at the top of the needle 80 circumference opposite from where the bendable portion of the needle is placed. In the present embodiment, there is an outer sleeve 80*o*, best shown in FIG. 11D, and the actuator 84 lies between the sleeve 80*o* and the needle surface 80*s*. In this embodiment, the needle is perforated as in other embodiments and a keel/rudder 80*k* exists; while the keel/rudder 80*k* is shown, in FIG. 11C as only part of the tip of the needle 80, it will be understood that this is due to the perforation being opposite the keel/rudder such that a full length keel/rudder would stiffen the needle opposite the bend zone thereby hampering the ability to steer this needle. A needle following the teachings of this embodiment can be created with no keel/rudder without departing from the novel scope of the present invention. It will be understood that the present invention can be made with an inner sleeve as well, without departing from the novel scope of the present invention. The perforations shown in the embodiment can be of any type of cut or slit or other opening into the needle surface at the bend location, including the kerf type openings discussed above.

In another embodiment, as shown in FIG. 12, a needle 90 can be provided with two wires to provide a higher control to the steerability of the needle. Similar to the prior embodiments, needle 90 is created with perforated segments on at least two points on the circumference of the needle—each having an actuation channel 90*c* created therein, as most clearly shown in FIG. 12D. A wire 90*w* can then be placed in both channels 90*c* and the user can then pull on one wire and push on (or in the case of a pre-tensioned wire, release the wire) the other to provide enhanced steerability. In a preferred embodiment, the channels are at a 180 degree distance from each other to provide the most control, but it will be understood that the channels, and subsequently the wires, can be placed at any points along the circumference to provide an enhanced steerability, of varying degree but perhaps with more comfort to the user, without departing from the novel scope of the present invention. Further, while the present embodiment incorporates two wires, additional wires can be incorporated and kerfing can be incorporated in a pattern that allows for additional wires to steer the needle in different directions. The present embodiment can be created with any of the features shown in the prior embodiments without departing from the novel scope of the present invention, including partial or full keels, inner and outer sleeves and the like. A better view of such a needle is shown in FIG. 13, where the wires 94 can be seen within the perforated section 90*p*.

In various embodiments of the present invention, steerability can be enhanced by the use of a split stylet 102, as shown in FIG. 14. In this embodiment, the needle 100 is made in a manner similar to those shown above with a flexible inner 100*i* and outer sleeve 100*o*. An introducer 104 is provided having a split wire such that when the halves of the introducer are moved relative to one another the needle is caused to bend. The needle again is perforated 100*p*, as before, and the stylet 102 is castellated in the bending region to allow for bending. In this embodiment, the needle is the actuation channel and a rudder or keel is either not required or can be incorporated as well to aid in steerability.

FIG. 15 shows a pre-bent needle 110 with the stylet 112, also pre-bent, it will be understood that a needle that can bend in one direction can be used herein as well. In the use of the present embodiment, the rotation of the stylet so that the bending force is in the same direction of pre-bend causes the needle to bend. After the bend is achieved, the stylet is removed and a syringe or other device can be attached to perform the necessary medical step for the patient. In a final illustrative embodiment, as shown in FIG. 16, a pre-bent inner needle 120 is shown within a straight outer needle. The inner needle is slideable within the outer needle and when placed in a body, the inner needle can be pushed out from the outer needle, the bend can then be steered as desired, past impediments, to the place where treatment is targeted. It will be seen that the needle and stylet can have bends that oppose each other such that the insertion of the stylet within the needle will cause the system of needle and stylet to become straightened (as the corresponding bends cancel each other out). Further, by twisting a stylet within the needle, the cancellation can be attenuated to provide the degree of bend needed by the user.

Although an illustrative embodiment of the invention has been shown and described, it is to be understood that various modifications and substitutions may be made by those skilled in the art without departing from the novel spirit and scope of the invention.

What is claimed is:

1. A needle system comprising a pre-bent needle having a bend and a pre-bent stylet having a bend, configured such that when the stylet is placed inside the needle, forming a combined longitudinal axis, the bend of the stylet and the bend of the needle are in opposition and the needle and stylet form a combined needle and stylet being generally unbent along the combined longitudinal axis; and wherein, when the pre-bent stylet and the pre-bent needle are rotated relative to one another, by turning one or the other of the needle or stylet relative to the other, along their combined longitudinal axis, the needle system is caused to bend.

* * * * *